(12) United States Patent
Xiao et al.

(10) Patent No.: US 11,452,502 B2
(45) Date of Patent: Sep. 27, 2022

(54) METHOD AND DEVICE FOR ACQUIRING BIOMECHANICAL PARAMETERS BASED ON ULTRASONIC ELASTOMYOGRAM

(71) Applicant: Shenzhen Institutes of Advanced Technology, Guangdong (CN)

(72) Inventors: Yang Xiao, Shenzhen (CN); Hairong Zheng, Shenzhen (CN); Congzhi Wang, Shenzhen (CN); Lili Niu, Shenzhen (CN); Zhiting Deng, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 150 days.

(21) Appl. No.: 16/482,802

(22) PCT Filed: Dec. 26, 2017

(86) PCT No.: PCT/CN2017/118725
§ 371 (c)(1),
(2) Date: Aug. 1, 2019

(87) PCT Pub. No.: WO2019/114034
PCT Pub. Date: Jun. 20, 2019

(65) Prior Publication Data
US 2020/0229794 A1 Jul. 23, 2020

(30) Foreign Application Priority Data

Dec. 12, 2017 (CN) .......................... 201711322506.4

(51) Int. Cl.
*A61B 8/08* (2006.01)
(52) U.S. Cl.
CPC ................ *A61B 8/485* (2013.01); *A61B 8/08* (2013.01); *A61B 8/5207* (2013.01)

(58) Field of Classification Search
CPC .......... A61B 8/485; A61B 8/08; A61B 8/5207
See application file for complete search history.

(56) References Cited

U.S. PATENT DOCUMENTS

| 2008/0004522 A1 | 1/2008 | Finni et al. |
| 2009/0177084 A1 | 7/2009 | Matsumura et al. |
| (Continued) | | |

FOREIGN PATENT DOCUMENTS

| CN | 102920485 A | 2/2013 |
| CN | 103584884 A | 2/2014 |
| (Continued) | | |

OTHER PUBLICATIONS

A. Arampatzis, et al, "Strain and elongation of the human gastrocnemius tendon and aponeurosis during maximal plantarflexion effort," Journal of Biomechanics, vol. 38, pp. 833-841, Apr. 2004 (Year: 2004).*

(Continued)

*Primary Examiner* — Oommen Jacob
*Assistant Examiner* — Nyrobi Celestine

(57) ABSTRACT

A method and a device for acquiring biomechanical parameters based on an ultrasonic elastomyogram are provided, wherein the method includes: synchronously collecting a dynamic myodynamics image sequence and a dynamic elasticity image sequence of a single skeletal muscle under continuous stretching; acquiring a myodynamics parameter corresponding to each myodynamics image in the dynamic myodynamics image sequence and an elasticity modulus value corresponding to each elasticity image in the dynamic elasticity image sequence respectively; and generating an ultrasonic elastomyogram curve with the myodynamics parameter as the abscissa and the synchronized elasticity modulus value as the ordinate, and estimating a muscle biomechanical parameter based on the ultrasonic elastomyogram curve. Dynamically changing biomechanical param- (Continued)

eters can be obtained, and the obtained muscle biomechanical parameters have relatively high accuracy.

11 Claims, 5 Drawing Sheets

(56) References Cited

U.S. PATENT DOCUMENTS

| | | | |
|---|---|---|---|
| 2010/0240994 | A1 | 9/2010 | Zheng |
| 2015/0011895 | A1 | 1/2015 | Johnstone et al. |

FOREIGN PATENT DOCUMENTS

| | | | |
|---|---|---|---|
| CN | 103690192 | A | 4/2014 |
| CN | 104622511 | A | 5/2015 |
| CN | 105997079 | A | 10/2016 |
| CN | 106175831 | A | 12/2016 |
| CN | 106202739 | A | 12/2016 |
| CN | 106264573 | A | 1/2017 |
| CN | 106821308 | A | 6/2017 |
| CN | 106890009 | A | 6/2017 |
| JP | 2009219834 | A | 10/2009 |

OTHER PUBLICATIONS

S. F. Eby, et al, "Validation of shear wave elastography in skeletal muscle," Journal of Biomechanics, vol. 46, pp. 2381-2387, Jul. 2013 (Year: 2013).*

L. A. Chernak, et al, "Length and activation dependent variations in muscle shear wave speed," Physiological Measurment, vol. 34, pp. 713-721, May 2013 (Year: 2013).*

T. K. Koo, et al, "Quantifying the passive stretching response of human tibialis anterior muscle using shear wave elastography," Clinical Biomechanics, vol. 29, pp. 33-39, Nov. 2013 (Year: 2013).*

Z. J. Zhang, et al, "Shear Elastic Modulus on Patellar Tendon Captured from Supersonic Shear Imaging: Correlation with Tangent Traction Modulus Computed from Material Testing System and Test-Retest Reliability," PLoS ONE, vol. 8, No. 6, pp. 1-9, Jun. 2013 (Year: 2013).*

M. Nakamura, et al, "Acute effects or static stretching on muscle hardness or the medial gastrocnemius muscle belly in humans: an ultrasonic shear-wave elastography study," Ultrasound in Medicine & Biology, vol. 40, No. 9, pp. 1991-1997, Mar. 2014 (Year: 2014).*

J. Gennisson et al., "Human muscle hardness assessment during incremental isometric contraction using transient elastography," Journal of Biomechanics, vol. 38, pp. 1543-1550, Aug. 2005 (Year: 2005).*

M. Shinohara, et al, "Real-time visualization of muscle stiffness distribution with ultrasound shear wave imaging during muscle contraction," Muscle & Nerve, pp. 1-4, Mar. 2010 (Year: 2010).*

M. M. Doyley, "Model-based elastography: a survey of approaches to the inverse elasticity problem," Physics in Medicine and Biology, vol. 57, pp. R35-R73, Jan. 2012 (Year: 2012).*

M. Nakamura et al, "Acute effects of static stretching on muscle hardness of the medial gastrocnemius muscle belly in humans: an ultrasonic shear-wave elastography study," Ultrasound in Medicine & Biology, vol. 40, No. 9, pp. 1991-1997, Mar. 2014 (Year: 2014).*

L. F.d. Oliveira et al, "In vivo passive mechanical properties estimation of Achilles tendon using ultrasound," Journal of Biomechanics, vol. 49, pp. 507-513, Oct. 2015 (Year: 2015).*

China Intellectual Property Office, Search Report for CN patent application No. 201711322506.4, dated May 23, 2019, 4 pages.

* cited by examiner

METHOD AND DEVICE FOR ACQUIRING BIOMECHANICAL PARAMETERS BASED ON ULTRASONIC ELASTOMYOGRAM

PRIORITY

This application is a U.S national application of the international application number PCT/CN2017/118725 filed on Dec. 26, 2017 and claiming priority of CN national application 201711322506.4 filed on Dec. 12, 2017 the contents of all of which are incorporated herein by reference.

TECHNICAL FIELD

The present disclosure relates to the technical field of testing, and particularly to a method and a device for acquiring biomechanical parameters based on an ultrasonic elastomyogram.

BACKGROUND ART

Muscles are important tissues that make up the human body, which account for 40%-45% of body weight. Muscles are classified into three types, i.e., skeletal muscles, smooth muscles and cardiac muscles, distributed around various organs and bones, with different structures, mechanical properties and functions. The musculoskeletal system relies on the binding force of muscles in order to keep stable and relies on the driving force of muscles in order to form behavior movements, and plays a vital role in human motions.

At present, testing on muscle biomechanical parameters is mainly based on ultrasonic shear wave elastography technique. Ultrasonic shear wave elastography technique realizes authentic quantitative measurement of the elasticity of muscle tissues, and its basic principle is: generating shear waves in the vicinity of a focal position by radiation force generated by an ultrasonic transducer, then measuring the propagation velocity of the shear waves in the tissues and calculating the elasticity modulus of the tissues.

However, in the prior art, muscle biomechanical parameters are mainly measured based on ultrasonic shear wave elastography technique in the following ways: (1) measuring the elasticity modulus values of skeletal muscles in relaxed state, and performing an evaluation through the difference of elasticity modulus values only, wherein muscles are the power source of human body to perform various motions, the muscle force will cause changes of elasticity modulus during motions, and the elasticity modulus values of the muscles in the relaxed state can only reflect the hardness when the muscle strength is zero and cannot fully characterize the biomechanical properties of the muscles; (2) measuring the elasticity modulus values of skeletal muscles in the relaxed state and in the tension state (active contraction) respectively, in order to evaluate the function and tension of the muscles, but muscle strength produced by active contraction is difficult to perform quantitative evaluation; or (3) measuring the elasticity modulus values of skeletal muscles at different joint angles, and studying the biomechanical properties of muscle tissues in the tension state, however, different joint angles are still qualitative index parameters, which vary from person to person and cannot be used for quantitative evaluation of muscle strength.

In conclusion, the existing method for testing muscle biomechanical parameters based on ultrasonic shear wave elastography technique is unable to acquire dynamic information and unable to acquire the same in a quantitative manner; therefore, the accuracy of the obtained muscle biomechanical parameters is not high.

SUMMARY

In view of the above, an object of the present disclosure is to provide a method and a device for testing muscle biomechanical parameters, so as to acquire dynamically changing biomechanical parameters and improve the accuracy of the obtained muscle biomechanical parameters.

In a first aspect, an example of the present disclosure provides a method for acquiring biomechanical parameters based on an ultrasonic elastomyogram, comprising:

synchronously collecting a dynamic myodynamics image sequence and a dynamic elasticity image sequence of a single skeletal muscle under continuous stretching;

acquiring a myodynamics parameter corresponding to each myodynamics image in the dynamic myodynamics image sequence and an elasticity modulus value corresponding to each elasticity image in the dynamic elasticity image sequence respectively; and generating an ultrasonic elastomyogram curve with the myodynamics parameter as the abscissa and the synchronized elasticity modulus value as the ordinate, and estimating a muscle biomechanical parameter based on the ultrasonic elastomyogram curve.

In connection with the first aspect, an example of the present disclosure provides a first feasible embodiment of the first aspect, in which the myodynamics image includes a displacement image, the myodynamics parameter includes a muscle stretching length, and before the synchronously collecting a dynamic myodynamics image sequence and a dynamic elasticity image sequence of a single skeletal muscle under continuous stretching, the method further comprises:

determining a feature point of a muscle tissue stretched end of the single skeletal muscle in an initial state; and calculating a distance from the feature point to the opposite end of the muscle tissue stretched end of the single skeletal muscle to obtain an initial length of the skeletal muscle.

In connection with the first feasible embodiment of the first aspect, an example of the present disclosure provides a second feasible embodiment of the first aspect, in which the determining a feature point of a muscle tissue stretched end of the single skeletal muscle comprises:

controlling an ultrasonic diagnostic apparatus to scan, in an imaging mode, a longitudinal section of the single skeletal muscle along a muscle bundle direction, and taking a detected junction between the single skeletal muscle and a tendon as the feature point.

In connection with the first feasible embodiment of the first aspect or the second feasible embodiment of the first aspect, an example of the present disclosure provides a third feasible embodiment of the first aspect, in which the acquiring a myodynamics parameter corresponding to each myodynamics image in the dynamic myodynamics image sequence comprises:

acquiring an effective value of a displacement change of the feature point relative to the position of the feature point in the initial state in the displacement image; and recording the sum of the initial length and the effective value of the displacement change as a muscle stretching length corresponding to the displacement image.

In connection with the third feasible embodiment of the first aspect, an example of the present disclosure provides a fourth feasible embodiment of the first aspect, in which the acquiring an effective value of a displacement change of the feature point relative to the position of the feature point in the initial state in the displacement image comprises:

controlling a myoelectric apparatus to monitor a myoelectric signal of the single skeletal muscle and the surrounding muscle groups; and taking the displacement change relative to the position of the feature point in the initial state in the displacement image as the effective value, when the amplitude of the myoelectric signal is smaller than a preset value.

In connection with the first aspect, an example of the present disclosure provides a fifth feasible embodiment of the first aspect, in which before the synchronously collecting a dynamic myodynamics image sequence and a dynamic elasticity image sequence of a single skeletal muscle under continuous stretching, the method further comprises:

determining a muscle belly position of the single skeletal muscle so as to collect the dynamic elasticity image sequence at the muscle belly position.

In connection with the fifth feasible embodiment of the first aspect, an example of the present disclosure provides a sixth feasible embodiment of the first aspect, in which the determining a muscle belly position of the single skeletal muscle comprises:

controlling the ultrasonic diagnostic apparatus to scan, in the imaging mode, a cross section of the skeletal muscle perpendicular to the muscle bundle direction, and taking the position with the largest cross section as the muscle belly position of the single skeletal muscle.

In connection with the fifth feasible embodiment of the first aspect or the sixth feasible embodiment of the first aspect, an example of the present disclosure provides a seventh feasible embodiment of the first aspect, in which the acquiring an elasticity modulus value corresponding to each dynamic elasticity image in the dynamic elasticity image sequence comprises:

outputting, at the muscle belly position of the single skeletal muscle and in the muscle bundle direction, the dynamic elasticity image sequence of the skeletal muscle under continuous stretching; and controlling the ultrasonic diagnostic apparatus to perform, in an analysis mode, quantitative analysis on a preset area of each elasticity image in the dynamic elasticity image sequence to obtain an elasticity modulus value corresponding to each elasticity image.

In connection with any one of the first aspect to the second feasible embodiment of the first aspect, the fifth feasible embodiment of the first aspect or the sixth feasible embodiment of the first aspect, an example of the present disclosure provides an eighth feasible embodiment of the first aspect, in which after the generating an ultrasonic elastomyogram curve with the myodynamics parameter as the abscissa and the synchronized elasticity modulus value as the ordinate, and before the estimating a muscle biomechanical parameter based on the ultrasonic elastomyogram curve, the method further comprises:

determining whether the ultrasonic elastomyogram curve accords with a preset mechanical model curve, and if yes, performing the step of estimating a muscle biomechanical parameter based on the ultrasonic elastomyogram curve.

In connection with the eighth feasible embodiment of the first aspect, an example of the present disclosure provides a ninth feasible embodiment of the first aspect, in which the myodynamics image includes a displacement image, the myodynamics parameter includes a muscle stretching length, and the estimating a muscle biomechanical parameter based on the ultrasonic elastomyogram curve comprises:

acquiring a model formula corresponding to the ultrasonic elastomyogram curve and each parameter in the model formula;

determining, according to the parameters, the length of the single skeletal muscle in the relaxed state, an elasticity modulus value corresponding to the length of the single skeletal muscle in the relaxed state, and an extension degree of the single skeletal muscle, the extension degree being a difference between the maximum stretching length of the single skeletal muscle and the length of the single skeletal muscle in the relaxed state; and applying the Gauss-Newton iterative method to the model formula to determine a hardness index of the single skeletal muscle, when the length of the skeletal muscle is larger than the length of the single skeletal muscle in the relaxed state.

In a second aspect, an example of the present disclosure provides a device for acquiring muscle biomechanical parameters based on an ultrasonic elastomyogram, comprising:

a collection module configured to synchronously collect a dynamic myodynamics image sequence and a dynamic elasticity image sequence of a single skeletal muscle under continuous stretching;

an acquisition module configured to acquire a myodynamics parameter corresponding to each myodynamics image in the dynamic myodynamics image sequence and an elasticity modulus value corresponding to each elasticity image in the dynamic elasticity image sequence respectively; and a determination module configured to generate an ultrasonic elastomyogram curve with the myodynamics parameter as the abscissa and the synchronized elasticity modulus value as the ordinate, and estimate a muscle biomechanical parameter based on the ultrasonic elastomyogram curve.

Compared with the prior art, in the examples of the present disclosure, a dynamic myodynamics image sequence and a dynamic elasticity image sequence of a single skeletal muscle under continuous stretching are synchronously collected, thereby a myodynamics parameter corresponding to each myodynamics image in the myodynamics image sequence and an elasticity modulus value corresponding to each dynamic elasticity image in the dynamic elasticity image sequence are acquired respectively, and an ultrasonic elastomyogram curve is generated with the myodynamics parameter as the abscissa and the synchronized elasticity modulus value as the ordinate, and a muscle biomechanical parameter is estimated based on the ultrasonic elastomyogram curve. Thus, the myodynamics parameters and elasticity modulus values obtained in the present disclosure are varying parameters of a single skeletal muscle measured during continuous stretching, an ultrasonic elastomyogram curve is generated finally, the biomechanical parameters of the single skeletal muscle during continuous stretching can be estimated based on the curve, and the biomechanical parameters thus obtained are dynamic and quantitative.

In order to make it easier to understand the objects, features and advantages of the present disclosure described above, detailed description is made below in connection with preferred embodiments with reference to the accompanying drawings.

BRIEF DESCRIPTION OF DRAWINGS

In order to more clearly illustrate the technical solutions of the embodiments of the present disclosure, brief description is made below on the drawings required to be used in the embodiments. It should be understood that the following drawings only illustrate some of the embodiments of the present disclosure and shall not be regarded as a limitation to the scope, and for a person of ordinary skills in the art, other related drawings may be obtained from these drawings without inventive effort.

DETAILED DESCRIPTION OF EMBODIMENTS

Figure 1:
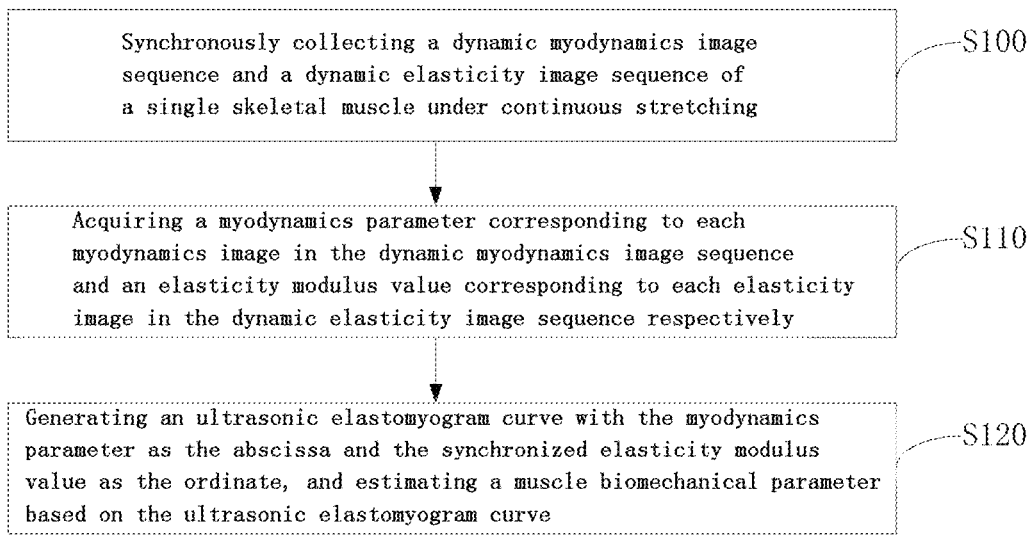
FIG. 1 is a flowchart of a method for acquiring muscle biomechanical parameters based on an ultrasonic elastomyogram according to an embodiment of the present disclosure.

In order to make the objects, technical solutions and advantages of the embodiments of the present disclosure clearer, the technical solutions of the embodiments of the present disclosure will be described clearly and completely below with reference to the drawings of the embodiments of the present disclosure. Apparently, the embodiments described are merely some of the embodiments of the present disclosure, rather than all of the embodiments. The components of the embodiments of the present disclosure described and illustrated in the drawings herein can generally be arranged and designed in a variety of different configurations. Thus, the following detailed description of the embodiments of the present disclosure provided in the drawings is not intended to limit the scope of the present disclosure claimed, but is merely representative of the selected embodiments of the present disclosure. All the other embodiments that are obtained by a person skilled in the art without inventive effort on the basis of the embodiments of the present disclosure shall be covered by the protection scope of the present disclosure.

EXAMPLE 1

Example 1 of the present disclosure provides a method for acquiring muscle biomechanical parameters based on an ultrasonic elastomyogram. The method flowchart thereof is as shown in FIG. 1, and the specific steps are as follows:

S100, synchronously collecting a dynamic myodynamics image sequence and a dynamic elasticity image sequence of a single skeletal muscle under continuous stretching.

The synchronous collection here means that each myodynamics image corresponds to one elasticity image, i.e., making the elasticity modulus value acquired later vary with the myodynamics parameters.

S110, acquiring a myodynamics parameter corresponding to each myodynamics image in the dynamic myodynamics image sequence and an elasticity modulus value corresponding to each elasticity image in the dynamic elasticity image sequence respectively.

S120, generating an ultrasonic elastomyogram curve with the myodynamics parameter as the abscissa and the synchronized elasticity modulus value as the ordinate, and estimating a muscle biomechanical parameter based on the ultrasonic elastomyogram curve.

In the above, the myodynamics parameters may include a muscle stretching length, a muscle strength, a strain and a joint angle, etc. The corresponding myodynamics image sequence may include a displacement image sequence, a muscle strength image sequence, a strain image sequence and a joint angle image sequence. Detailed description is made taking a displacement image sequence as an example in an embodiment of the present disclosure.

Figure 2:
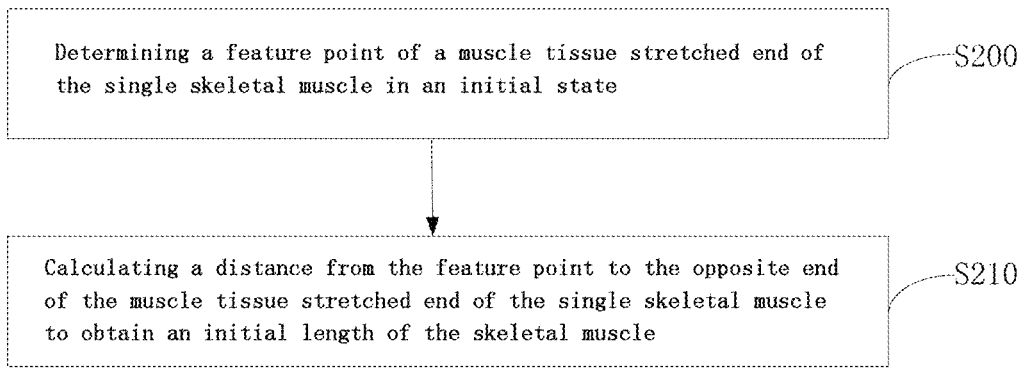
FIG. 2 is a flowchart of a method for acquiring an initial length of a skeletal muscle according to an embodiment of the present disclosure.

In a preferred embodiment, in the technical solution proposed in example 1 of the present disclosure, the myodynamics image includes a displacement image, the myodynamics parameter includes a muscle stretching length, and in step S100, i.e., before the synchronously collecting a dynamic myodynamics image sequence and a dynamic elasticity image sequence of a single skeletal muscle under continuous stretching, the method further comprises the following steps, and the flowchart is as shown in FIG. 2:

S200, determining a feature point of a muscle tissue stretched end of the single skeletal muscle in an initial state.

This requires that the testee refrains from strenuous activities within 2 hours prior to the test, to ensure that the feature point of a muscle tissue stretched end of a single skeletal muscle of the testee in an initial state can be collected.

Optionally, the determining a feature point of a muscle tissue stretched end of the single skeletal muscle comprises:

controlling an ultrasonic diagnostic apparatus to scan, in an imaging mode, a longitudinal section of the single skeletal muscle along a muscle bundle direction, and taking a detected junction between the single skeletal muscle and a tendon as the feature point.

S210, calculating a distance from the feature point to the opposite end of the muscle tissue stretched end of the single skeletal muscle to obtain an initial length of the skeletal muscle.

The initial length here refers to the length of the single skeletal muscle before stretching, that is, the feature point is located at one end point of the two ends of the single skeletal muscle, and the initial length is the length from one end point of the single skeletal muscle to the opposite end point thereof.

Figure 3:
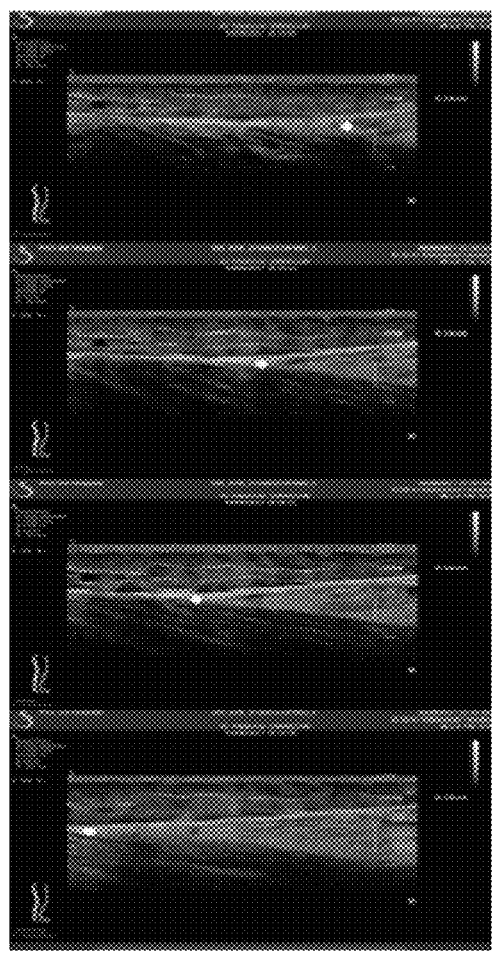
FIG. 3 is a displacement image sequence diagram according to an embodiment of the present disclosure.
Figure 4:
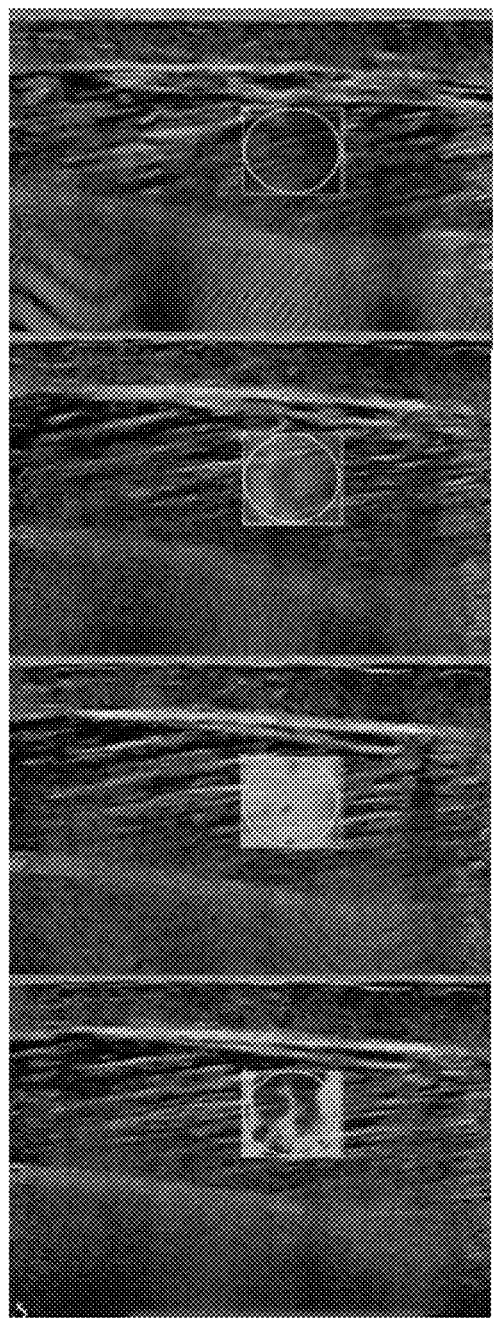
FIG. 4 is an elasticity modulus sequence diagram according to an embodiment of the present disclosure.

FIG. 3 shows a displacement image sequence acquired in the test and FIG. 4 shows an elasticity image sequence synchronously obtained from the test.

Figure 5:
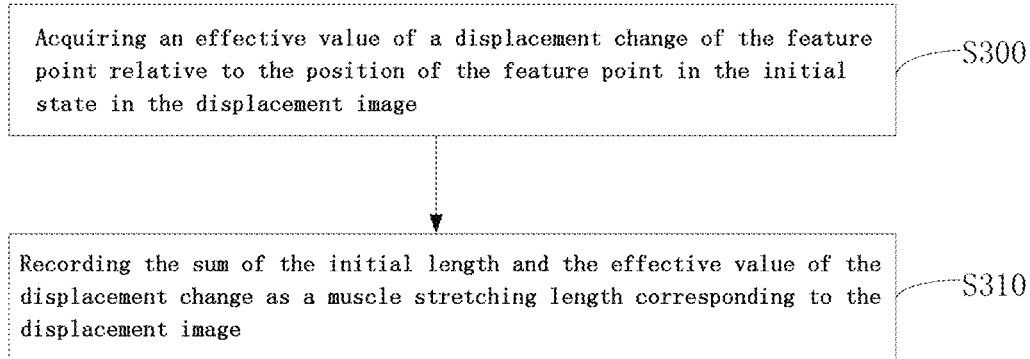
FIG. 5 is a flowchart of a method for acquiring a muscle stretching length of a skeletal muscle according to an embodiment of the present disclosure.

In a preferred embodiment, in the technical solution proposed in example 1 of the present disclosure, in step S110, i.e., the acquiring a myodynamics parameter corresponding to each myodynamics image in the dynamic myodynamics image sequence comprises the following steps, and the flowchart is as shown in FIG. 5:

S300, acquiring an effective value of a displacement change of the feature point relative to the position of the feature point in the initial state in the displacement image.

In the above, the acquiring an effective value of a displacement change of the feature point relative to the position of the feature point in the initial state in the displacement image comprises:

controlling a myoelectric apparatus to monitor a myoelectric signal of the single skeletal muscle and the surrounding muscle groups; and taking the displacement change relative to the position of the feature point in the initial state in the displacement image as the effective value, when the amplitude of the myoelectric signal is smaller than a preset value.

In order to prevent the occurrence of false images due to unconscious active contraction of the muscles of the testee, during the test, the myoelectric signals of the tested single skeletal muscle and the surrounding muscle groups are collected for monitoring. When the amplitude of the myoelectric signals is less than 1% of the amplitude of the myoelectric signals when the muscles experience the maximum contraction, it is determined that the collected displacement changes are recorded as effective values.

S310, recording the sum of the initial length and the effective value of the displacement change as a muscle stretching length corresponding to the displacement image.

If the initial length is denoted as $l_{init}$ and the effective value of the displacement change is denoted $\Delta l$, the muscle stretching length l is calculated according to the following formula (1):

$$l = l_{init} + \Delta l \qquad (1)$$

In a preferred embodiment, in the technical solution proposed in example 1 of the present disclosure, in step S100, i.e., before the synchronously collecting a dynamic myodynamics image sequence and a dynamic elasticity image sequence of a single skeletal muscle under continuous stretching, the method further comprises:

determining a muscle belly position of the single skeletal muscle so as to collect the dynamic elasticity image sequence at the muscle belly position.

The muscle belly position of the single skeletal muscle is determined in the following manner:

controlling the ultrasonic diagnostic apparatus to scan, in the imaging mode, a cross section of the skeletal muscle perpendicular to the muscle bundle direction, and taking the position with the largest cross section as the muscle belly position of the single skeletal muscle.

In the embodiments of the present disclosure, the ultrasonic diagnostic apparatus is controlled in the imaging mode to scan the cross section perpendicular to the muscle bundle of the skeletal muscle to be tested, the probe of the ultrasonic diagnostic apparatus is rotated at the position corresponding to the maximum cross section, the long axis of the skeletal muscle is examined along the longitudinal section in the muscle bundle direction, the elastic imaging mode is started to acquire the elasticity modulus value corresponding to each elasticity image in the dynamic elasticity image sequence.

Figure 6:
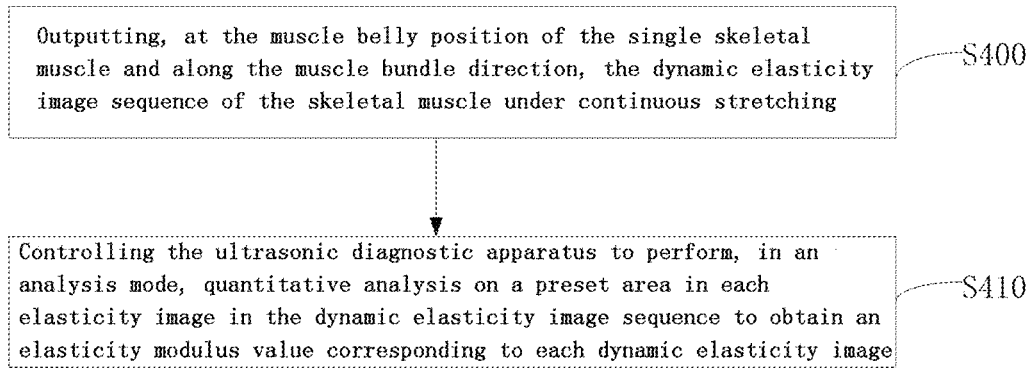
FIG. 6 is a flowchart for obtaining an elasticity modulus value corresponding to each dynamic elasticity image according to an embodiment of the present disclosure.

In the above, the acquiring an elasticity modulus value corresponding to each elasticity image in the elasticity image sequence comprises the following steps, and the flowchart thereof is as shown in FIG. 6:

S400, outputting, at the muscle belly position of the single skeletal muscle and along the muscle bundle direction, the dynamic elasticity image sequence of the skeletal muscle under continuous stretching; and S410, controlling the ultrasonic diagnostic apparatus to perform, in an analysis mode, quantitative analysis on a preset area in each elasticity image in the dynamic elasticity image sequence to obtain an elasticity modulus value corresponding to each dynamic elasticity image.

After the ultrasonic diagnostic apparatus is controlled to locate the muscle belly position of the skeletal muscle, the elastic imaging mode is started and the probe position is fixed, and the dynamic elasticity image sequence of the tested skeletal muscle under continuous stretching is output according to a preset frequency. As shown in FIG. 4, after the region of interest, i.e., the test region, for example, the region of 10 mm×10 mm, of each elasticity image is determined, the analysis mode of the ultrasonic diagnostic apparatus is started to perform quantitative analysis on the region, and then the elasticity modulus value corresponding to each elasticity image is output.

Preferably, at the time of measuring the muscle stretching length of the single skeletal muscle to be measured and the elasticity modulus value corresponding to the muscle stretching length, in order to reduce the measurement error, it is feasible to perform several measurements and take the mean value of the several measurements as the final measurement result, for example, the measurement may be performed 3 times.

In a preferred embodiment, in the technical solution proposed in example 1 of the present disclosure, in step S120, i.e., after the generating an ultrasonic elastomyogram curve with the myodynamics parameter as the abscissa and the synchronized elasticity modulus value as the ordinate, and before the estimating a muscle biomechanical parameter based on the ultrasonic elastomyogram curve, the method further comprises:

determining whether the ultrasonic elastomyogram curve accords with a preset mechanical model curve, and if yes, performing the step of estimating a muscle biomechanical parameter based on the ultrasonic elastomyogram curve.

After an ultrasonic elastomyogram curve is generated with the muscle stretching length as the abscissa and the elasticity modulus value as the ordinate, whether the curve accords with a preset mechanical model curve is determined according to the shape of the curve, and when it is determined that the curve accords with the preset mechanical model curve, the subsequent step of estimating a muscle biomechanical parameter based on the ultrasonic elastomyogram curve is performed.

Figure 7:
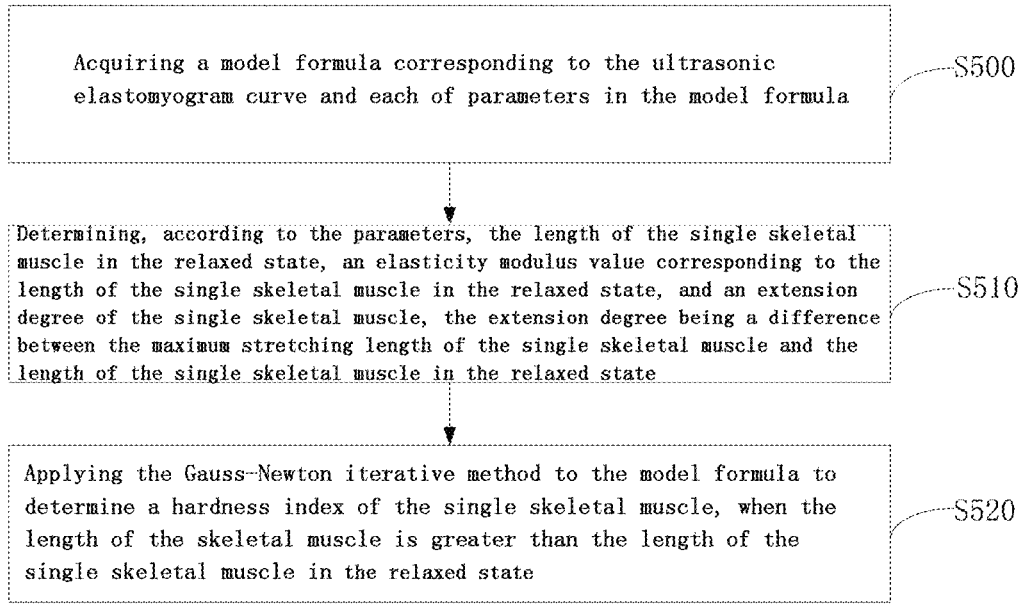
FIG. 7 is a flowchart of a method for estimating muscle biomechanical parameters according to an embodiment of the present disclosure.

In a preferred embodiment, in the technical solution proposed in example 1 of the present disclosure, the myodynamics image includes a displacement image, the myodynamics image includes a displacement image, and in step S120, the estimating a muscle biomechanical parameter based on the ultrasonic elastomyogram curve comprises the following steps, and the flowchart is as shown in FIG. 7:

S500, acquiring a model formula corresponding to the ultrasonic elastomyogram curve and each parameter in the model formula;

S510, determining, according to the parameters, the length of the single skeletal muscle in the relaxed state, an elasticity modulus value corresponding to the length of the single skeletal muscle in the relaxed state, and an extension degree of the single skeletal muscle, the extension degree being a difference between the maximum stretching length of the single skeletal muscle and the length of the single skeletal muscle in the relaxed state; and S520, applying the Gauss-Newton iterative method to the model formula to determine a hardness index of the single skeletal muscle, when the length of the skeletal muscle is greater than the length of the single skeletal muscle in the relaxed state.

The relaxed state of the single skeletal muscle refers to a state in which the muscle strength is zero in the process of stretching the single skeletal muscle from the initial state, and the elasticity modulus of the single skeletal muscle is almost unchanged in the relaxed state.

Figure 8:
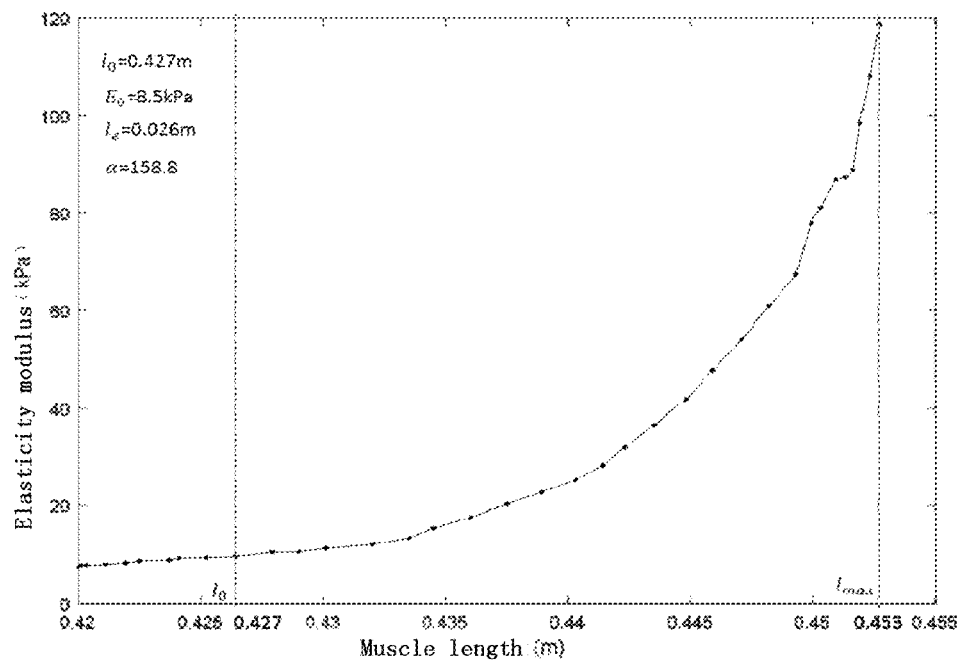
FIG. 8 is a schematic diagram of an elastomyogram curve according to an embodiment of the present disclosure.

The ultrasonic elastomyogram curve generated by taking the muscle stretching length as the abscissa and the elasticity modulus value as the ordinate is as shown in FIG. 8, and the obtained model formula corresponding to the ultrasonic elastomyogram curve is as shown in the following formula (2):

$$E = E_q; l \leq l_g;$$

$$E = k(\theta^{\alpha(l-l_0)} - 1) + E_0; l > l_0 \quad (2)$$

In the above formula, $E_0$ is the muscle tissue relaxed elasticity modulus value, $l_0$ is the muscle relaxed length, $\alpha$ is the hardness index, and k is the proportionality coefficient. The elasticity modulus value corresponding to the ordinate in the elastomyogram curve keeps unchanged when the muscle is in the relaxed state, and the abscissa length corresponding to the change node at which the elasticity modulus value is significantly increased, i.e., muscle strength occurs, is taken as the estimated value of $l_0$, as shown in FIG. 8; the mean value of $E_{mean}$ of all measured elasticity moduli corresponding to the interval where the abscissa is less than $l_0$ in the elastomyogram is taken as the estimated value of $E_0$, as shown in FIG. 8; the extension degree $l_e$ is defined as the measured maximum stretching length $l_{max} - l_0$; and $\alpha$ needs to be estimated from the sequence interval ($l \geq l_0$) where the abscissa is greater than or equal to $l_0$, and the specific steps are as follows:

$$\text{making } y = f(x, \alpha) = [k(e^{\alpha(x-l_g)} - 1) + E_0]; \quad (3)$$

where the unknown parameter that needs to be estimated is $a = [\alpha, k]$, the least square determination principle is used, the iterative method based on Taylor series is employed, and the initial test coefficient is denoted as $a^0$, i.e.:

$$y = f(x, a^0); \quad (4)$$

The initial parameter usually does not satisfy the condition that the quadratic sum of the error is minimum, the quadratic sum of the error is minimized by adjusting the coefficient $a^0$, and the improved coefficient is denoted as $a^1$, then there is obtained:

$$a^1 = a^0 + \Delta a; \quad (5)$$

Substituting formula (5) into formula (4) produces:

$$y = f(x, a^1) = f(x, a^0 + \Delta a); \quad (6)$$

The function is expanded according to Taylor series, and the first order derivative term is retained, then there is obtained:

$$y \approx f(x, a^0) + \sum_{k=0}^{l} \Delta a_k [\partial f / \partial a_k]^0; \quad (7)$$

Making $f_i^0 = f(x_i, a^0)$, the error between it and $y_i$ is:

$$\varepsilon_j = y_i - f_i^0 - \sum_{k=0}^{l} \Delta a_k [\partial f / \partial a_k]^0; i = 1, 2, \ldots, n \quad (8)$$

The quadratic sum of the error is:

$$S = \sum_{i=0}^{n} \left\{ y_i - f_i^0 - \sum_{k=0}^{l} \Delta a_k \left[ \frac{\partial f_i}{\partial a_k} \right]^0 \right\}^2; \quad (9)$$

The minimum value of the quadratic sum of the error needs to be calculated, then:

$$\frac{\partial S}{\partial (\Delta a_p)} = -2 \sum_{i=0}^{n} \left\{ y_i - f_i^0 - \sum_{k=0}^{l} \Delta a_k \left[ \frac{\partial f_i}{\partial a_k} \right]^0 \right\} \left[ \frac{\partial f_i}{\partial a_p} \right]^0 = 0; \quad (10)$$

$$p = 0, 1$$

i.e., $$\sum_{i=0}^{n} (y_i - f_i^0) \left[ \frac{\partial f_i}{\partial a_p} \right]^0 = \sum_{k=0}^{l} \Delta a_k \left\{ \sum_{i=0}^{n} \left[ \frac{\partial f_i}{\partial a_k} \right]^0 \left[ \frac{\partial f_i}{\partial a_p} \right]^0 \right\}; p = 0, 1 \quad (11)$$

It can be represented by matrix notation as:

$$K(\Delta a) = b \quad (12)$$

where the element of $\Delta a$ is $\Delta a_p (p=0,1)$ and:

$$K_{pk} = \sum_{i=0}^{n} \left[ \frac{\partial f_i}{\partial a_k} \right]^0 \left[ \frac{\partial f_i}{\partial a_p} \right]^0 \quad (13)$$

$$b_p = \sum_{i=0}^{n} (y_i - f_i^0) \left[ \frac{\partial f_i}{\partial a_p} \right]^0; p, k = 0, 1; \quad (14)$$

In the above equation set, $\Delta a$ is solved by Gaussian elimination method, then the value of $a^1$ is calculated, finally, the above steps are repeated with the calculated $a^1$ as the initial value, to repeatedly iterate and correct the value of $\Delta a$ until the norm of $\Delta a$ is less than a specified threshold.

FIG. 8 is an elastomyogram of a normal human gastrocnemius muscle, with the stretching length of a single skeletal muscle as the abscissa and the corresponding elasticity modulus value as the ordinate, from which it is estimated that the muscle relaxed elasticity modulus $E_0 = 8.5$ kPa, the relaxed length $l_0 = 0.427$ m, the extension degree $l_e = 0.026$ m, and the hardness index $\alpha = 158.8$.

EXAMPLE 2

Figure 9:
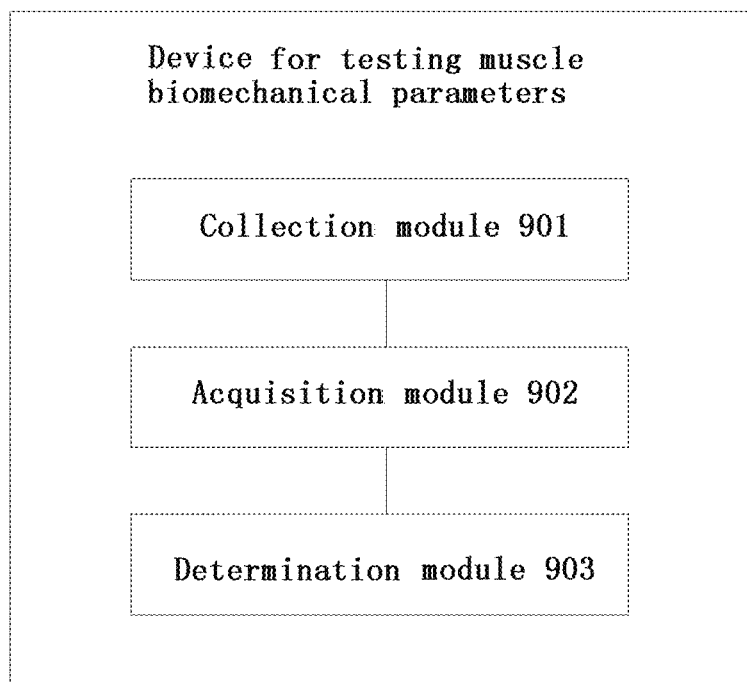
FIG. 9 is a schematic structural diagram of a device for acquiring muscle biomechanical parameters based on an ultrasonic elastomyogram according to an embodiment of the present disclosure.

Example 2 of the present disclosure provides a device for acquiring muscle biomechanical parameters based on an ultrasonic elastomyogram, which, as shown in FIG. 9, comprises a collection module 901, an acquisition module 902 and a determination module 903.

The collection module 901 is configured to synchronously collect a dynamic myodynamics image sequence and a dynamic elasticity image sequence of a single skeletal muscle under continuous stretching.

The acquisition module 902 is configured to acquire a myodynamics parameter corresponding to each myodynamics image in the dynamic myodynamics image sequence and an elasticity modulus value corresponding to each elasticity image in the dynamic elasticity image sequence respectively.

The determination module 903 is configured to generate an ultrasonic elastomyogram curve with the myodynamics parameter as the abscissa and the synchronized elasticity modulus value as the ordinate, and estimate a muscle biomechanical parameter based on the ultrasonic elastomyogram curve.

Preferably, the myodynamics image includes a displacement image, the myodynamics parameter includes a muscle stretching length, and before synchronously collecting a dynamic myodynamics image sequence and a dynamic elasticity image sequence of a single skeletal muscle under continuous stretching, the collection module 901 is further configured to:

determine a feature point of a muscle tissue stretched end of the single skeletal muscle in an initial state; and calculate a distance from the feature point to the opposite end of the muscle tissue stretched end of the single skeletal muscle to obtain an initial length of the skeletal muscle.

Preferably, the collection module 901 is specifically configured to:

control an ultrasonic diagnostic apparatus to scan, in an imaging mode, a longitudinal section of the single skeletal muscle along a muscle bundle direction, and take a detected junction between the single skeletal muscle and a tendon as the feature point.

Preferably, the acquisition module 902 is specifically configured to:

acquire an effective value of a displacement change of the feature point relative to the position of the feature point in the initial state in the displacement image; and record the sum of the initial length and the effective value of the displacement change as a muscle stretching length corresponding to the displacement image.

Preferably, the acquisition module 902 determines the effective value in the following manner:

controlling a myoelectric apparatus to monitor a myoelectric signal of the single skeletal muscle and the surrounding muscle groups; and taking the displacement change relative to the position of the feature point in the initial state in the displacement image as the effective value, when the amplitude of the myoelectric signal is smaller than a preset value.

Preferably, before synchronously collecting a dynamic myodynamics image sequence and a dynamic elasticity image sequence of a single skeletal muscle under continuous stretching, the collection module 901 is further configured to:

determine a muscle belly position of the single skeletal muscle so as to collect the dynamic elasticity image sequence at the muscle belly position.

Preferably, the collection module 901 determines a muscle belly position of the single skeletal muscle specifically in the following manner:

controlling the ultrasonic diagnostic apparatus to scan, in the imaging mode, a cross section of the skeletal muscle perpendicular to the muscle bundle direction, and taking the position with the largest cross section as the muscle belly position of the single skeletal muscle.

Preferably, the acquisition module 902 acquires an elasticity modulus value specifically in the following manner:

outputting, at the muscle belly position of the single skeletal muscle and along the muscle bundle direction, the dynamic elasticity image sequence of the skeletal muscle under continuous stretching; and controlling the ultrasonic diagnostic apparatus to perform, in an analysis mode, quantitative analysis on a preset area in each elasticity image in the dynamic elasticity image sequence to obtain an elasticity modulus value corresponding to each dynamic elasticity image.

Preferably, after generating an ultrasonic elastomyogram curve with the myodynamics parameter as the abscissa and the synchronized elasticity modulus value as the ordinate, and before estimating a muscle biomechanical parameter based on the ultrasonic elastomyogram curve, the determination module 903 is further configured to:

determine whether the ultrasonic elastomyogram curve accords with a preset mechanical model curve, and if yes, perform the step of estimating a muscle biomechanical parameter based on the ultrasonic elastomyogram curve.

Preferably, the myodynamics image includes a displacement image, the myodynamics parameter includes a muscle stretching length, and the determination module 903 estimates a muscle biomechanical parameter in the following manner:

acquiring a model formula corresponding to the ultrasonic elastomyogram curve and each of parameters in the model formula;

determining, according to the parameters, the length of the single skeletal muscle in the relaxed state, an elasticity modulus value corresponding to the length of the single skeletal muscle in the relaxed state, and an extension degree of the single skeletal muscle, the extension degree being a difference between the maximum stretching length of the single skeletal muscle and the length of the single skeletal muscle in the relaxed state; and applying the Gauss-Newton iterative method to the model formula to determine a hardness index of the single skeletal muscle, when the length of the skeletal muscle is greater than the length of the single skeletal muscle in the relaxed state.

Compared with the prior art, in the embodiments of the present disclosure, a dynamic myodynamics image sequence and a dynamic elasticity image sequence of a single skeletal muscle under continuous stretching are synchronously collected, a myodynamics parameter corresponding to each myodynamics image in the myodynamics image sequence and an elasticity modulus value corresponding to each dynamic elasticity image in the dynamic elasticity image sequence are acquired separately, and an ultrasonic elastomyogram curve is generated with the myodynamics parameter as the abscissa and the synchronized elasticity modulus value as the ordinate, and a muscle biomechanical parameter is estimated based on the ultrasonic elastomyogram curve. Thus, the myodynamics parameters and elasticity modulus values obtained in the embodiments of the present disclosure are varying parameters of a single skeletal muscle measured during continuous stretching, an ultrasonic elastomyogram curve is generated finally, the biomechanical parameters of the single skeletal muscle during continuous stretching can be estimated based on the curve, and the biomechanical parameters thus obtained are dynamic and quantitative.

A computer program product of the method for acquiring muscle biomechanical parameters based on an ultrasonic elastomyogram provided by the embodiments of the present disclosure comprises a computer readable storage medium storing program codes that comprise instructions for executing the methods described in the preceding method embodiments. As to the specific implementation, reference can be made to the method embodiments, and no further description will be made herein.

The device for acquiring muscle biomechanical parameters based on an ultrasonic elastomyogram provided by the embodiments of the present disclosure may be specific hardware on the equipment or software or firmware installed on the equipment, etc. The device provided by the embodiments of the present disclosure has the same implementation principle and technical effects as those described in the foregoing method embodiments. For the sake of brevity, as to the contents not mentioned in the part of the device embodiments, reference can be made to the corresponding contents in the preceding method embodiments. It could be clearly understood by those skilled in the art that for convenience and brevity of description, as to the specific working processes of the system, device and unit described above, reference can be made to the corresponding processes in the method embodiments described above, and no further description will be made herein.

In the embodiments provided in the present disclosure, it should be understood that the disclosed device and method can be implemented in other ways. The device embodiments described above are merely exemplary, for example, the classification of the units is merely classification according to logical functions, and in actual implementation, the units can be classified in other ways. In another example, multiple units or components may be combined or integrated into another system, or some features may be omitted, or not executed. In addition, the mutual coupling, direct coupling or communication connection illustrated or discussed may be indirect coupling or communication connection through some communication interfaces, devices or units, and may be in electrical, mechanical, or other form.

The unit described as a separate component may or may not be physically separated, and the component shown as a unit may or may not be a physical unit, that is, it may be located in one place, or may also be distributed to multiple network units. Some or all of the units may be selected according to actual needs to achieve the objects of the solutions of the embodiments.

In addition, the functional units in the embodiments of the present disclosure can be integrated in one processing unit, or each physically exists separately, or two or more units can be integrated in one unit.

When implemented in the form of software functional units and sold or used as independent products, the functions can be stored in a computer readable storage medium. Based on such understanding, the substance of the technical solution of the present disclosure, in another words, the part of the technical solution of the present disclosure that makes contributions to the prior art, or part of the technical solution can be embodied in the form of a software product, and the computer software product is stored in a storage medium, comprising some instructions for enabling one computer device (which can be a personal computer, a server, a network device or the like) to execute all or some of the steps of the methods in the embodiments of the present disclosure. The storage medium includes various mediums capable of storing program codes, such as a USB flash disk, a mobile hard disk, a Read-Only Memory (ROM), a Random Access Memory (RAM), a magnetic disk, or an optical disk.

It should be noted that similar reference signs and letters denote similar items in the drawings, and therefore, once a certain item is defined in one figure, it does not need to be further defined or explained in the subsequent figures; moreover, the terms such as "first", "second" and "third" are only used for differentiated description and cannot be understood as indication or implication of relative importance.

Finally, it should be noted that the above embodiments are only particular embodiments of the present disclosure and are used to illustrate the technical solutions of the present disclosure, rather than limit the same, and the scope of protection of the present disclosure is not limited thereto; although the present disclosure has been described in detail with reference to the foregoing embodiments, it should be understood by a person of ordinary skills in the art that within the technical scope disclosed in the present discourse, a person skilled in the art could still modify the technical solutions described in the embodiments, readily conceive variations thereof, or make equivalent substitution to some of the technical features therein; and the modifications, variations or substitutions would not cause the substance of the corresponding technical solutions to depart from the spirit and scope of the technical solutions of the embodiments of the present disclosure, but shall covered by the scope of protection of the present disclosure. Therefore, the scope of protection of the present disclosure shall be determined by the scope of protection of the appended claims.

The invention claimed is:

1. A method for acquiring a muscle biomechanical parameter based on an ultrasonic elastomyogram, comprising:
synchronously collecting a dynamic myodynamics image sequence and a dynamic elasticity image sequence of a single skeletal muscle under continuous stretching;
acquiring a myodynamics parameter corresponding to each myodynamics image in the dynamic myodynamics image sequence and an elasticity modulus value corresponding to each elasticity image in the dynamic elasticity image sequence respectively; and
generating an ultrasonic elastomyogram curve, with the myodynamics parameter as the abscissa and the synchronized elasticity modulus value as the ordinate, and estimating the muscle biomechanical parameter based on the ultrasonic elastomyogram curve;
wherein after the generating an ultrasonic elastomyogram curve with the myodynamics parameter as the abscissa and the synchronized elasticity modulus value as the ordinate, and before the estimating a muscle biomechanical parameter based on the ultrasonic elastomyogram curve, the method further comprises:
determining whether the ultrasonic elastomyogram curve matches with a preset mechanical model curve, and if the ultrasonic elastomyogram curve matches with the preset mechanical model curve, performing the operation of estimating a muscle biomechanical parameter based on the ultrasonic elastomyogram curve;
wherein the myodynamics image comprises a displacement image, the myodynamics parameter comprises a muscle stretching length, and the estimating a muscle biomechanical parameter based on the ultrasonic elastomyogram curve comprises:
acquiring a model formula corresponding to the ultrasonic elastomyogram curve and each of parameters in the model formula as follows:

$$E=E_0; l \leq l_0;$$

$$E=k(e^{\alpha(l-l_0)}-1)+E_0; l>l_0$$

where $E_0$ represents a relaxed elasticity modulus value of the single skeletal muscle, $l_0$ represents a relaxed length of the single skeletal muscle, $\alpha$ represents a hardness index i.e. the muscle biomechanical parameter of the single skeletal muscle to be solved for, e represents the natural number, l represents the length of the single skeletal muscle when it is being stretched, and k is a proportionality coefficient;
determining, according to the parameters, the length of the single skeletal muscle in the relaxed state, the elasticity modulus value corresponding to the length of the single skeletal muscle in the relaxed state, and an extension degree of the single skeletal muscle, wherein the extension degree is a difference between a maximum stretching length of the single skeletal muscle and the length of the single skeletal muscle in the relaxed state; and applying Gauss-Newton iterative method to the model formula to determine the hardness index of the single skeletal muscle, when the length of the skeletal muscle is greater than the length of the single skeletal muscle in the relaxed state.

2. The method according to claim 1, wherein before the synchronously collecting a dynamic myodynamics image sequence and a dynamic elasticity image sequence of a single skeletal muscle under continuous stretching, the method further comprises:

determining a feature point of a muscle tissue stretched end of the single skeletal muscle in an initial state; and calculating a distance from the feature point to an opposite end of the muscle tissue stretched end of the single skeletal muscle to obtain an initial length of the skeletal muscle.

3. The method according to claim 2, wherein the determining a feature point of a muscle tissue stretched end of the single skeletal muscle comprises:

controlling an ultrasonic diagnostic apparatus to scan, in an imaging mode, a longitudinal section of the single skeletal muscle along a muscle bundle direction, with a detected junction between the single skeletal muscle and a tendon as the feature point.

4. The method according to claim 2, wherein the acquiring a myodynamics parameter corresponding to each myodynamics image in the dynamic myodynamics image sequence comprises:

acquiring an effective value of a displacement change of the feature point relative to a position of the feature point in the initial state in the displacement image; and recording a sum of the initial length and the effective value of the displacement change, as a muscle stretching length corresponding to the displacement image.

5. The method according to claim 4, wherein the acquiring an effective value of a displacement change of the feature point relative to a position of the feature point in the initial state in the displacement image comprises:

controlling a myoelectric apparatus to monitor myoelectric signals of the single skeletal muscle and surrounding muscle groups; and using, as the effective value, the displacement change relative to the position of the feature point in the initial state in the displacement image, when an amplitude of the myoelectric signal is smaller than a preset value.

6. The method according to claim 1, wherein before the synchronously collecting a dynamic myodynamics image sequence and a dynamic elasticity image sequence of a single skeletal muscle under continuous stretching, the method further comprises:

determining a muscle belly position of the single skeletal muscle so as to collect the dynamic elasticity image sequence at the muscle belly position.

7. The method according to claim 6, wherein the determining a muscle bel position of the single skeletal muscle comprises:

controlling the ultrasonic diagnostic apparatus to scan, in an imaging mode, a cross section of the skeletal muscle perpendicular to the muscle bundle direction, with a position with largest cross section as the muscle belly position of the single skeletal muscle.

8. The method according to claim 6, wherein the acquiring an elasticity modulus value corresponding to each dynamic elasticity image in the dynamic elasticity image sequence comprises:

outputting, at the muscle belly position of the single skeletal muscle and along the muscle bundle direction, the dynamic elasticity image sequence of the skeletal muscle under continuous stretching; and controlling the ultrasonic diagnostic apparatus to perform, in an analysis mode, quantitative analysis on a preset area in each elasticity image in the dynamic elasticity image sequence to obtain an elasticity modulus value corresponding to each elasticity image.

9. A device for acquiring a muscle biomechanical parameter based on an ultrasonic elastomyogram, the device comprising a processor and a non-transitory computer-readable storage medium storing program instructions executable by the processor, wherein the program instructions when executed by the processor cause the device to perform the following operations:

synchronously collecting a dynamic myodynamics image sequence and a dynamic elasticity image sequence of a single skeletal muscle under continuous stretching;

acquiring a myodynamics parameter corresponding to each myodynamics image in the dynamic myodynamics image sequence and an elasticity modulus value corresponding to each elasticity image in the dynamic elasticity image sequence respectively; and generating an ultrasonic elastomyogram curve with the myodynamics parameter as the abscissa and the synchronized elasticity modulus value as the ordinate, and estimate a muscle biomechanical parameter based on the ultrasonic elastomyogram curve;

wherein after the generating an ultrasonic elastomyogram curve with the myodynamics parameter as the abscissa and the synchronized elasticity modulus value as the ordinate, and before the estimating a muscle biomechanical parameter based on the ultrasonic elastomyogram curve, the program instructions when executed by the processor further cause the device to perform the following operations:

determining whether the ultrasonic elastomyogram curve matches with a preset mechanical model curve, and if the ultrasonic elastomyogram curve matches with the preset mechanical model curve, perform the operation of estimating a muscle biomechanical parameter based on the ultrasonic elastomyogram curve;

wherein the myodynamics image comprises a displacement image, the myodynamics parameter comprises a muscle stretching length, and the estimating the muscle biomechanical parameter based on the ultrasonic elastomyogram curve comprises:

acquiring a model formula corresponding to the ultrasonic elastomyogram curve and each of parameters in the model formula as follows:

$$E=E_0; l \leq l_0;$$

$$E=k(e^{\alpha(l-l_0)}-1)+E_0; l > l_0$$

where $E_0$ represents a relaxed elasticity modulus value of the single skeletal muscle, $l_0$ represents a relaxed length of the single skeletal muscle, $\alpha$ represents a hardness index i.e. the muscle biomechanical parameter of the single skeletal muscle to be solved for, e represents the natural number, l represents the length of the single skeletal muscle when it is being stretched, and k is a proportionality coefficient;

determining, according to the parameters, the length of the single skeletal muscle in the relaxed state, the elasticity modulus value corresponding to the length of the single skeletal muscle in the relaxed state, and an extension degree of the single skeletal muscle, wherein the extension degree is a difference between a maximum stretching length of the single skeletal muscle and the length of the single skeletal muscle in the relaxed state; and applying Gauss-Newton iterative method to the model formula to determine a hardness index of the single skeletal muscle, when the length of the skeletal muscle is greater than the length of the single skeletal muscle in the relaxed state.

10. The method according to claim 3, wherein the acquiring a myodynamics parameter corresponding to each myodynamics image in the dynamic myodynamics image sequence comprises:

acquiring an effective value of a displacement change of the feature point relative to a position of the feature point in the initial state in the displacement image; and recording a sum of the initial length and the effective value of the displacement change, as a muscle stretching length corresponding to the displacement image.

11. The method according to claim 7, wherein the acquiring an elasticity modulus value corresponding to each dynamic elasticity image in the dynamic elasticity image sequence comprises:

outputting, at the muscle belly position of the single skeletal muscle and along the muscle bundle direction, the dynamic elasticity image sequence of the skeletal muscle under continuous stretching; and controlling the ultrasonic diagnostic apparatus to perform, in an analysis mode, quantitative analysis on a preset area in each elasticity image in the dynamic elasticity image sequence to obtain an elasticity modulus value corresponding to each elasticity image.

* * * * *